United States Patent [19]

Nakane

[11] Patent Number: 4,588,741

[45] Date of Patent: May 13, 1986

[54] PLATELET AGGREGATION INHIBITING AND BRONCHOCONSTRICTION INHIBITING THIABICYCLOHEPTANE SUBSTITUTED AMINO PROSTAGLANDIN ANALOG DERIVATIVES, COMPOSITIONS, AND METHOD OF USE THEREFOR

[75] Inventor: Masami Nakane, Hopewell, N.J.

[73] Assignee: E. R. Squibb & Sons, Inc., Princeton, N.J.

[21] Appl. No.: 706,813

[22] Filed: Feb. 28, 1985

[51] Int. Cl.[4] ............ A61K 31/38; C07D 495/08
[52] U.S. Cl. .................... 514/443; 549/58
[58] Field of Search ............ 549/58, 463; 514/443, 514/469

[56] References Cited

U.S. PATENT DOCUMENTS

| 4,143,054 | 3/1979 | Sprague | 260/346.22 |
|---|---|---|---|
| 4,187,236 | 2/1980 | Sprague | 260/346.22 |
| 4,220,594 | 9/1980 | Sprague | 260/345.9 |
| 4,228,180 | 10/1980 | Sprague | 424/285 |
| 4,254,044 | 3/1981 | Sprague | 260/347.8 |
| 4,416,896 | 11/1983 | Nakane et al. | 424/285 |
| 4,456,615 | 6/1984 | Nakane et al. | 424/285 |
| 4,456,617 | 6/1984 | Nakane et al. | 424/285 |
| 4,526,901 | 7/1985 | Nakane | 549/463 |

FOREIGN PATENT DOCUMENTS

| 0043292 | 8/1982 | European Pat. Off. | 424/285 |
|---|---|---|---|
| 2039909 | 8/1980 | United Kingdom | 424/285 |
| 2133791 | 8/1984 | United Kingdom | 549/463 |

OTHER PUBLICATIONS

"New Synthetic Approaches to Symmetrical Sulfur--Bridged Carbocycles", by Corey et al., *The Journal of Organic Chemistry*, vol. 31, No. 6, pp. 1663-1668.

"Thiosteroids-XXVII[1] Steroidal Transannular 2α,5α--Episulphide-I. Synthesis of 5α-Cholestan-2α,5-Episulphide Derivatives", by Komeno et al., *Tetrahedron*, vol. 27, pp. 1503-1516.

*Primary Examiner*—Henry R. Jiles
*Assistant Examiner*—J. G. Mullins
*Attorney, Agent, or Firm*—Lawrence S. Levinson; Burton Rodney

[57] ABSTRACT

7-Thiabicycloheptane substituted amino prostaglandin analogs are provided having the structural formula

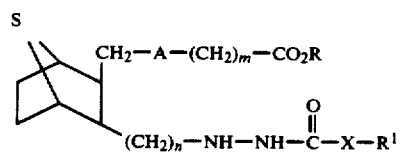

wherein R is hydrogen, lower alkyl, alkali metal, glucamine salt or trihydroxymethylaminomethane salt, $R^1$ is H (where $X \neq O$), lower alkyl, aryl, aralkyl, cycloalkyl or cycloalkylalkyl, $R^2$ is hydrogen or lower alkyl, A is $-CH=CH-$ or $-(CH_2)_2-$, n is 1 to 4, and m is 1 to 8, and including all stereoisomers thereof.

The compounds are cardiovascular agents useful, for example, in the treatment of thrombotic disease.

15 Claims, No Drawings

PLATELET AGGREGATION INHIBITING AND BRONCHOCONSTRICTION INHIBITING THIABICYCLOHEPTANE SUBSTITUTED AMINO PROSTAGLANDIN ANALOG DERIVATIVES, COMPOSITIONS, AND METHOD OF USE THEREFOR

DESCRIPTION OF THE INVENTION

The present invention relates to thiabicycloheptane substituted prostaglandin analogs which are cardiovascular agents useful, for example, in the treatment of thrombotic disease. These compounds have the structural formula

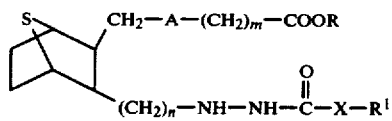

wherein

A is $CH_2-CH_2$ or $CH=CH-$; m is 1 to 8; R is H, lower alkyl, alkali metal or protonated polyhydroxylamine, such as tris(hydroxymethyl)aminomethane or glucamine; n is 1 to 4, X is O, $CH_2$ or NH; and $R^1$ is hydrogen (in which case X is $CH_2$ or NH), lower alkyl, aryl, aralkyl, cycloalkyl or cycloalkylalkyl.

Thus, compounds included within the scope of the present invention include:

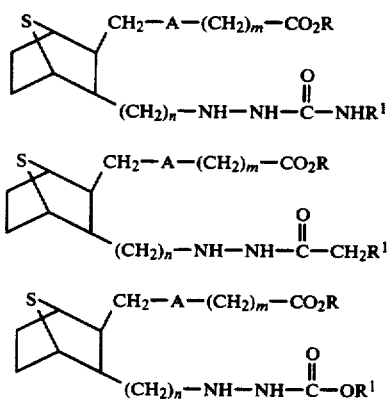

The term "lower alkyl" or "alkyl" as employed herein alone or as part of another group includes both straight and branched chain carbons, such as methyl, ethyl, propyl, isopropyl, butyl, t-butyl, isobutyl, pentyl, hexyl, isohexyl, heptyl, 4,4-dimethylpentyl, octyl, 2,2,4-trimethylpentyl, nonyl, decyl, undecyl, dodecyl, the various branched chain isomers thereof, and the like as well as such groups including a halo-substituent, such as F, Br, Cl or I or $CF_3$, an alkoxy substituent, an aryl substituent, an alkyl-aryl substituent, a haloaryl substituent, a cycloalkyl substituent, an alkylcycloalkyl substituent, hydroxy, an alkylamino substituent, an alkanoylamino substituent, an arylcarbonylamino substituent, a nitro substituent, a cyano substituent, a thiol substituent, or an alkylthio substituent.

The term "cycloalkyl" as employed herein alone or as part of another group includes saturated cyclic hydrocarbon groups containing 3 to 12 carbons, preferably 3 to 8 carbons, which include cyclopropyl, cyclobutyl, cyclopentyl, cyclohexyl, cycloheptyl, cyclooctyl, cyclodecyl and cyclododecyl, any of which groups may be substituted with 1 or 2 halogens, 1 or 2 lower alkyl groups 1 or 2 lower alkoxy groups. 1 or 2 hydroxy groups, 1 or 2 alkylamino groups, 1 or 2 alkanoylamino groups, 1 or 2 arylcarbonylamino groups, 1 or 2 amino groups, 1 or 2 nitro groups, 1 or 2 cyano groups, 1 or 2 thiol groups, and/or 1 or 2 alkylthio groups.

The term "aryl" or "Ar" as employed herein refers to monocyclic or bicyclic aromatic groups containing from 6 to 10 carbons in the ring portion, such as phenyl, naphthyl, substituted phenyl or substituted naphthyl wherein the substituent on either the phenyl or naphthyl may be 1 or 2 lower alkyl groups, halogens (Cl, Br or F), 1 or 2 lower alkoxy groups, 1 or 2 hydroxy groups, 1 or 2 alkylamino groups, 1 or 2 alkanoylamino groups, 1 or 2 arylcarbonylamino groups, 1 or 2 amino groups, 1 or 2 nitro groups, 1 or 2 cyano groups, 1 or 2 thiol groups, and/or 1 or 2 alkylthio groups.

The term "aralkyl", "aryl-alkyl" or "aryl-lower alkyl" as used herein alone or as part of another group refers to lower alkyl groups as discussed above having an aryl substituent, such as benzyl.

The term "lower alkoxy", "alkoxy" or "aralkoxy" as employed herein alone or as part of another group includes any of the above lower alkyl, alkyl or aralkyl groups linked to an oxygen atom.

The term "alkanoyl" as used herein as part of another group refers to lower alkyl linked to a carbonyl group.

The terms $(CH_2)_m$ and $(CH_2)_n$ includes straight or branched chain radicals having from 1 to 7 carbons in the normal chain and may contain one or more lower alkyl and/or halogen substituents. Examples of $(CH_2)_m$ and $(CH_2)_n$ groups include

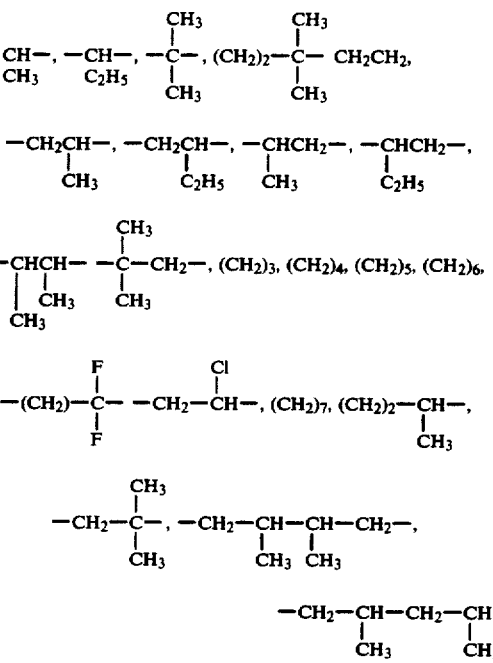

and the like.

The term "halogen" or "halo" as used herein refers to chlorine, bromine, fluorine or iodine with chlorine being preferred.

Preferred are those compounds of formula I wherein A is a $-CH=CH-$, m is 2 or 4, n is 1, R is H, X is NH, and $R^1$ is aryl such as phenyl, aralkyl such as benzyl or 1-methylbenzyl or cycloalkyl, such as cyclohexyl.

The compounds of formula I of the invention may be prepared as described below.

Compounds of the invention may be prepared according to the following reaction sequences employing aldehyde IV or IVA as a starting material.

Compound V is then reduced, such as by reacting V with a reducing agent, such as $NaBH_3CN$ or $NaBH_4$ in the presence of acetic acid to form compound VI (where A is CH=CH) or hydrogen with palladium on carbon as a catalyst to form compound VIA (where A is $(CH_2)_2$).

In the reaction sequence identified as "B" where in

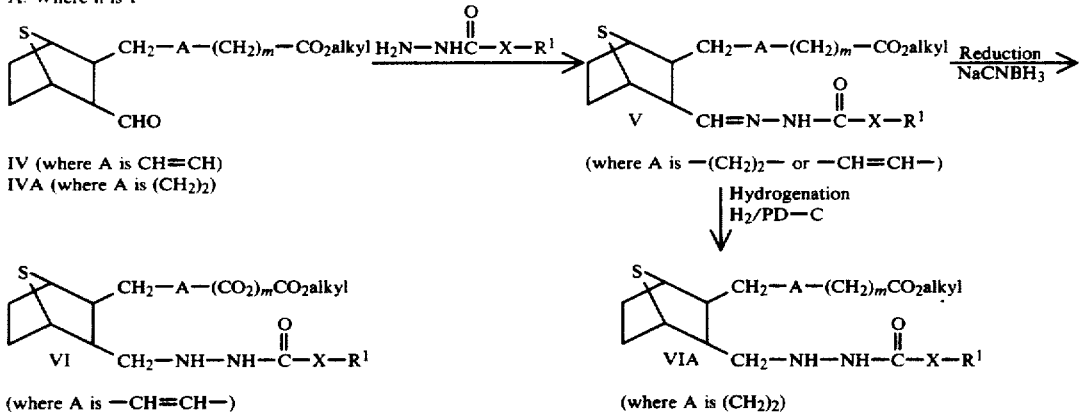

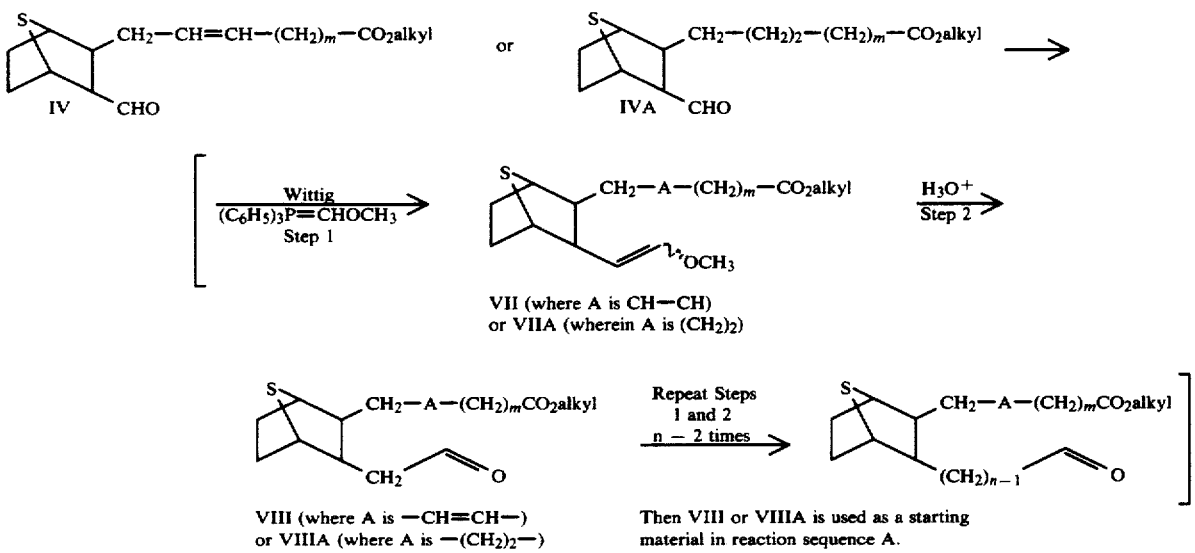

In the reaction sequence identified as "A", compounds of the invention wherein n is 1, that is,

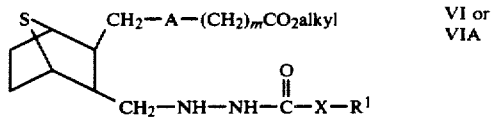

are prepared by reacting aldehyde IV or IVA with a hydrazine derivative $$H_2N-NH-\overset{O}{\overset{\|}{C}}-X-R^1$$

Z to form compound V, employing a molar ratio of IV or IVA:Z of within the range of from about 0.8:1 to about 1:1, in a protic solvent such as methanol or ethanol.

formula I n is 2 to 4, aldehyde IV or IVA is used to prepare aldehyde VII or VIIA (where n is 2–4) by carrying out a homologation sequence, such as a Wittig reaction with $(C_6H_5)_3P=CHOMe$ followed by hydrolysis, (n−1) times. The aldehyde VII or VIIA (where n is 2–4) is thus carried on to compounds of this invention where n is 2–4, that is

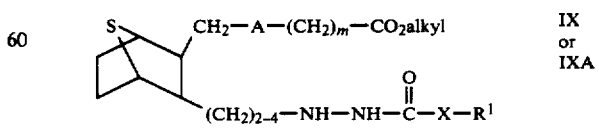

(IX where A is —CH=CH—)
(IXA where A is $(CH_2)_2$)
by employing aldehyde VII or VIIA in place of aldehyde IV or IVA in reaction sequence A.

Esters VI, VIA, IX or IXA may be hydrolyzed to the corresponding acid by treating the esters with an alkali metal hydroxide, such as lithium or sodium hydroxide in the presence of a solvent such as tetrahydrofuran, methanol or dimethoxyethane-water to form the alkali metal salt followed by neutralizing with an acid, such as dilute hydrochloric acid or oxalic acid to form the corresponding acid.

The tris(hydroxymethyl)aminomethane or glucamine salt of any of the acids of formula I of the present invention is formed by reacting a solution of such acid in a solvent such as methanol with tris(hydroxymethyl)aminomethane or glucamine and thereafter the solvent is removed by evaporation to leave the desired salt.

The starting aldehydes IV and IVA may be prepared according to the following reaction sequence.

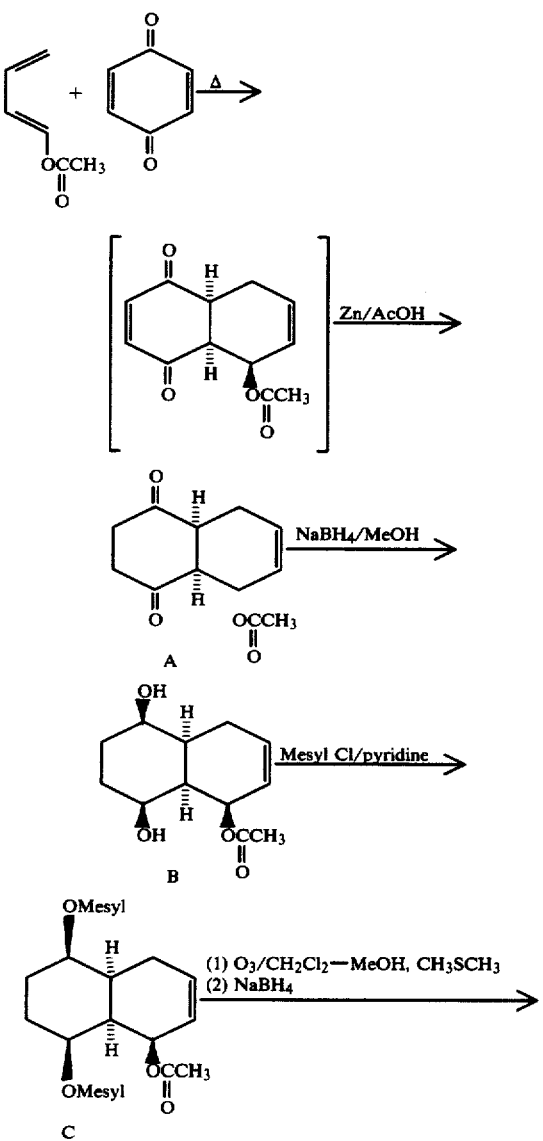

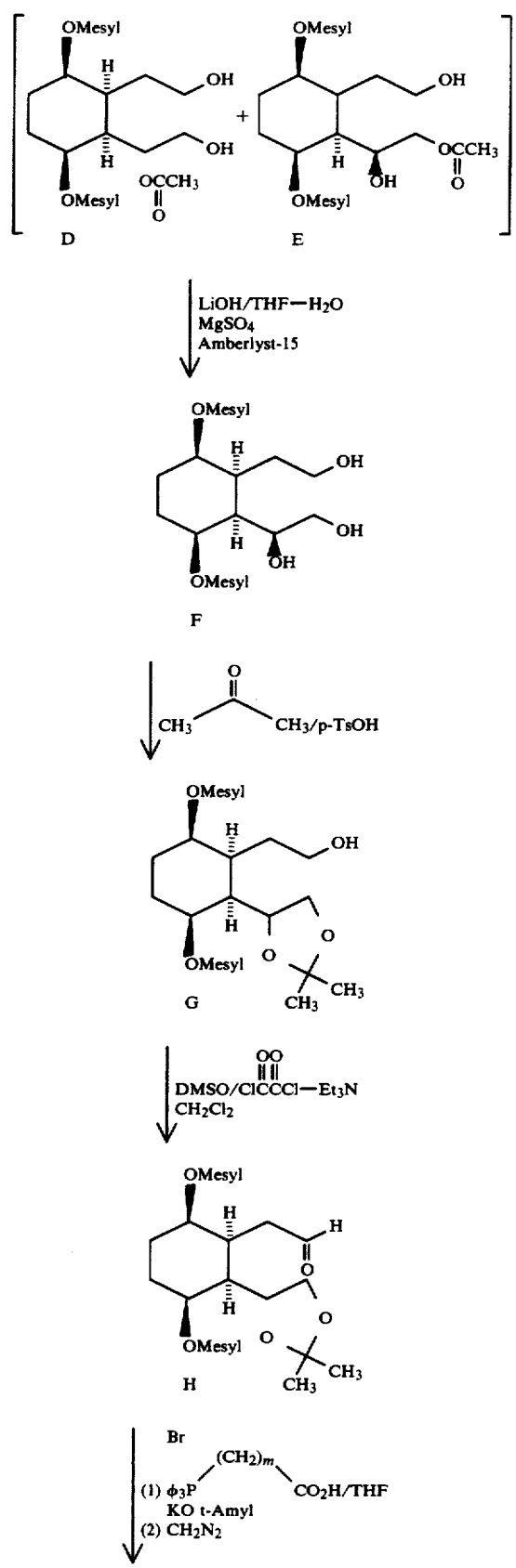

-continued

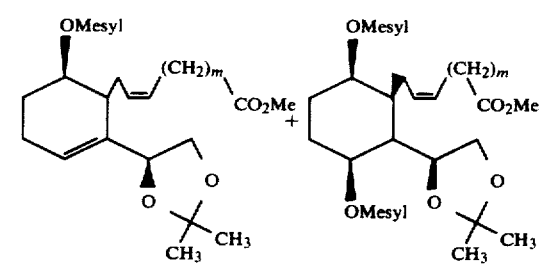

J ↓ MeOH/H⁺        J' ↓

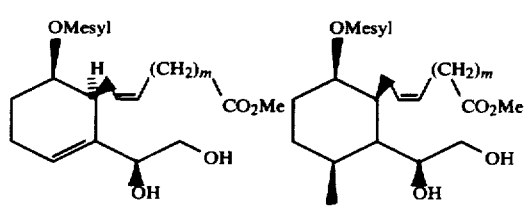

K          K'

NaIO₄/MeOH—H₂O

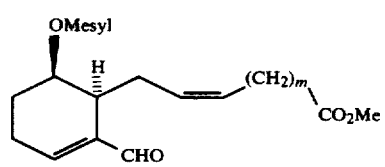

L (1) HSCCH₃/Et₃N
(2) MeOH/H⁺

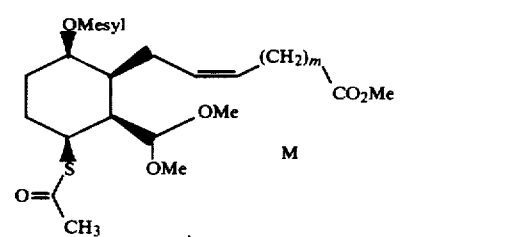

M

DBU/Toluene

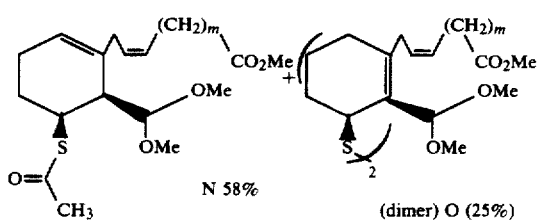

N 58%        (dimer) O (25%)

-continued (1) NaOMe/MeOH
(2) O₂/CuSO₄

↓

(dimer) O

SO₂Cl₂/CH₂Cl₂

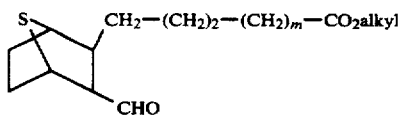

P

ZnCl₂/NaCNBH₃/Et₃N ↓

Q

H⁺/H₂CO/Acetone ↓

IV

The starting material where A is —(CH₂)₂—, i.e., $$\text{S} \diagdown \text{CH}_2-(CH_2)_2-(CH_2)_m-CO_2\text{alkyl} \qquad \text{IVA}$$
CHO may be prepared by hydrogenation of compound Q, followed by hydrolysis using a strong acid such as trifluoroacetic acid or methane sulfonic acid in acetone and 37% formaline.

Stereoisomeric forms of the compounds of the invention which may be made employing the procedures outlined above include

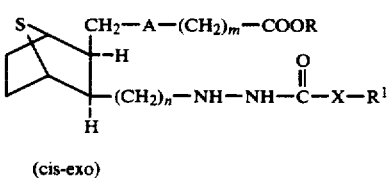

(cis-exo)

-continued

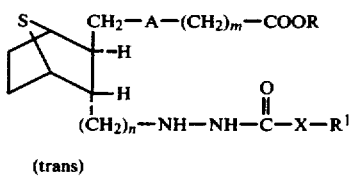

(trans)

The nucleus in each of the compounds of the invention is depicted as

for matter of convenience; it will also be appreciated that the nucleus in the compounds of the invention may be depicted as

The compounds of this invention are cardiovascular agents useful as platelet aggregation inhibitors, such as inhibiting arachidonic acid-induced platelet aggregation (e.g., for treatment of thrombotic disease, such as coronary or cerebral thromboses) and in inhibiting bronchoconstriction as induced by asthma. They are also selective thromboxane $A_2$ receptor antagonists and synthetase inhibitors, e.g., having a vasodilatory effect for treatment of myocardial ischemic disease, such as angina pectoris.

The compounds of the invention can be administered orally or parenterally to various mammalian species known to be subject to such maladies, e.g., humans, cats, dogs, and the like in an effective amount within the dosage range of about 1 to 100 mg/kg, preferably about 1 to 50 mg/kg and especially about 2 to 25 mg/kg on a regimen in single or 2 to 4 divided daily doses.

The compounds of the invention may also be administered topically to any of the above mammalian species in amounts of from about 0.1 to 10 mg/kg in single or 2 to 4 divided daily doses.

The active substance can be utilized in a composition such as tablet, capsule, solution or suspension containing about 5 to about 500 mg per unit of dosage of a compound or mixture of compounds of formula I. They may be compounded in conventional matter with a physiologically acceptable vehicle or carrier, excipient, binder, preservative, stabilizer, flavor, etc. as called for by accepted pharmaceutical practice. Also as indicated in the discussion above, certain members additionally serve as intermediates for other members of the group.

The following examples represent preferred embodiments of the present invention. Unless otherwise indicated, all temperatures are expressed in degrees Centigrade.

EXAMPLE 1

[1α,2β(5Z),3β,4α]-7-[3-[[2-[(phenylamino)carbonyl]hydrazino]methyl]-7-thiabicyclo[2.2.1]hept-2-yl]-5-heptenoic acid, methyl ester)

A.
(4aα,5β,8aα)-5-(Acetyloxy)-1,2,3,4,-4a,5,8,8a-octahydro-1,4-naphthalenedione 1-Acetoxy-1,3-butadiene (150 g, 1.338 mole) was added to p-quinone (131 g, 1.213 mole) in $CCl_4$ (100 ml) and diisopropyl ether (350 ml). The reaction was heated in a steam bath with occasional swirling, until the reaction became homogeneous. The reaction was allowed to cool to 35° C. The reaction was then heated at reflux for one hour and concentraed in vacuo. Zn dust (200 g) was added portionwise to a mechanically stirred solution of the resulting straw-colored oil in $Et_2O$ (100 ml) and glacial AcOH (500 ml) at 5°~10° C. The reaction was kept below 20° C. Stirring was continued for one hour at 5°~15° C. EtOAc (500 ml) was added to the reaction, which was filtered. The filter cake was washed with EtOAc (~800 ml). The filtrate was concentrated below 30° C. in vacuo to remove most of the acetic acid. The residue was dissoled in EtOAc (600 ml) and combined with the wash, which was washed with saturated $NaHCO_3$ (100 ml) and brine (200 ml×2). $NaHCO_3$ and brine washes were combined and re-extracted with EtOAc (400 ml). The EtOAc re-extract was washed with brine (100 ml×2). All the EtOAc layers were combined and dried over $MgSO_4$. Filtration and evaporation of solvent gave a straw-colored sludge. Diisopropyl ether (120 ml) was added and filtered. The resulting white powdery solids were washed again with diisopropyl ether (100 ml). The white solids (192 g) obtained were recrystallized from isopropyl alcohol (384 ml) to afford colorless crystals (178 g). The mother liquor and the diisopropyl ether washes were combined and crystallized in the same way to give addition crystals (30 g). Thus, the desired title compound (208 g, 0.937 mole, 77% from p-quinone) was obtained.

Cf J.O.C. (1964) 1341-1348, I. A. Kaye and R. S. Matthews.

B.
(1α,4α,4aβ,5α,8aβ)-1,2,3,4,4a,5,8,8a-Octahydro-1,4,5-naphthalenetriol, 5-acetate Part A compound (146 g, 0.657 mole) was dissolved in MeOH (1000 ml) and $CH_2Cl_2$ (500 ml). The reaction was cooled to −30° C.~−35° C., $NaBH_4$ (18.3 g, 0.495 mole) was added in portions under mechanical stirring. Stirring was continued for 2 hours at −30° C.~−35° C. after completion of the addition. The reaction was gradually warmed to −15° C. Then, $NH_4Cl$ solution ($NH_4Cl$, 35 g in $H_2O$, 150 ml) was added. The reaction was vigorously stirred for 30 minutes at −15° C., and concentrated in vacuo to ~400 ml. Brine (100 ml) and saturated $NH_4Cl$ (50 ml) were added to the residue. The products were extracted with EtOAc (1500 ml, 300 ml×2). The combined EtOAc layers were washed with brine (150 ml) and dried over $Na_2SO_4$. Filtration and evaporation of solvents gave a pale yellow oil (161 g), which was redissolved in MeOH (~300 ml) and concentrated to remove a possible impurity of boric acid. The resulting pale yellow oil (158 g) upon heating in diisopropyl ether (800 ml) under vigorous agitation, solidified. The solids were harvested, washed with diisopropyl ether (100 ml) to give white solids (116 g).

The mother liquor and the wash were combined, and concentrated in vacuo to ~400 ml. Colorless crystals (8.9 g) were obtained from the concentrate. Thus, the desired title diol compound (124.9, 0.553 mole, 84%) was obtained.

Cf J.O.C. (1964) 1341–1348. I. A. Kaye and R. S. Matthews.

C.
(1α,4α,4aβ,5α,8aβ)-1,2,3,4,4a,5,8,8a-Octahydro-1,4,5-naphthalenetriol, 5-acetyl-1,4-bis(methanesulfonate)

Part B diol (50 g, 0.221 mole) was suspended in pyridine (250 ml) and cooled to 0° C. Mesyl Cl (50 ml, 0.646 mole) was added dropwise. Stirring was continued at 0° C. for one hour. The reaction was gradually warmed to room temperature and left overnight. The reaction was poured into ice (~500 ml) and stirred for one hour. The resulting white precipitate was harvested and washed with water until the wash became neutral (~pH 5). The white solids were dried in a heated vacuum oven at 40° C.-50° C. The desired title dimesylate product (75 g, 0.196 mole, 88%) was obtained.

Cf J.O.C. (1964) 1341–1348, I. A. Kaye and R. S. Matthews.

D to F.
(1α,2β,3β,4α)-2-[(S*)-1,2-Dihydroxyethyl]-3-(2-hydroxyethyl)-1,4-cyclohexanediol, 1,4-bis(methanesulfonate) (F)

Part C dimesylate (72 g, 0.188 mole) was dissolved in $CH_2Cl_2$ (540 ml) and MeOH (208 ml). After the solution was cooled to −78° C., $O_3$ was introduced until the reaction became blue. An excess of $O_3$ was purged with a stream of $O_2$ for 20 minutes, followed by $N_2$ for 30 minutes. Dimethylsulfide (29.2 ml) was added and the reaction was warmed to −30° C. gradually. Additional MeOH (400 ml) was added and the reaction was stirred for 30 minutes at −30° C. Then $NaBH_4$ (14.8 g, 0.4 mole) was added portionwise over 20 minutes. The reaction was gradually warmed to −10° C. and stirred for one hour. $NH_4Cl$ (53 g) in $H_2O$ (150 ml) was added and the reaction was concentrated in vacuo to ~300 ml. Brine (100 ml) was added to the residue, which was extracted with EtOAC (800 ml, 400 ml×3). The combined EtOAc layers were dried over $MgSO_4$. Filtration and evaporation of solvents gave a colorless heavy oil (95 g). MeOH (300 ml) was added to the oil and the resulting homogeneous solution was concentrated to dryness to remove a possible impurity of boric acid. A pale yellow oil (81 g, a mixture of secondary acetate (D) and primary acetate (E)) was obtained. $LiOH.H_2O$ (15.8 g) dissolved in $H_2O$ (100 ml) was added to the oil (81 g) dissolved in THF (1300 ml). The reaction was mechanically stirred for 4 hours at room temperature. $MgSO_4$ (solid, 75 g) was added and the reaction was filtered. The filter cake was washed with THF (300 ml). The filtrate and the washes were combined and treated with Amberlyst-15 resin (35 g). The reaction was stirred for 5 minutes and filtered through Celite, which was washed with THF (200 ml). The filtrate and the washes were combined and concentrated in vacuo to give a viscous oil (61.5 g), which partially solidified upon stadning in a cold room. The resulting solid title triol was crystallized from isopropanol (210 ml) to give white solids (59.68 g, 0.159 mole, 84% from Part C dimesylate).

Anal Calcd for $C_{12}H_{24}O_9S_2$: C, 38.28; H, 6.42; S, 17.03; Found: C, 38.31, H, 6.46; S, 16.97.

G.
(1α,2β,3β,4α)-2-[(S*)-2,2-Dimethyl-1,3-dioxolan-4-yl]-3-(2-hydroxyethyl)-1,4-cyclohexanediol, 1,4-bis(methanesulfonate)

p-TsOH.$H_2O$ (260 mg, 0.00126 mole) was added to a magnetically stirred suspension of Part F triol (61 g, 0.162 mole) in acetone (1600 ml, dried over $B_2O_3$). The reaction became homogeneous in 30 minutes and stirring was continued overnight. 3A molecular sieve (30 g) was added and the reaction was stirred for an additional 2.5 hours. Then, $NaHCO_3$ (1.1 g, 0.0131 mole) in $H_2O$ (15 ml) was added. The reaction was filtered through a Celite pad, and concentrated in vacuo to give white solids (69 g). Slow addition of diisopropyl ether to the solids dissolved in hot acetone (100 ml) gave the title alcohol in the form of a white fine powder (65.5 g, 0.157 mole, 97%).

Anal Calcd for $C_{15}H_{28}O_9S_2$: C, 43.25; H, 6.77; S, 15.39; Found: C, 43.35; H, 6.84; S, 15.35.

H.
(1α,2α,3β,6β)-2-[(S*)-2,2-Dimethyl-1,3-dioxolan-4-yl]-3,6-bis[(methylsulfonyl)oxy]cyclohexaneacetaldehyde DMSO (5.08 ml) in $CH_2Cl_2$ (30 ml) was added dropwise to oxalyl chloride (2.296 ml) in $CH_2Cl_2$ (100 ml) at −78° C. The reaction was stirred at −78° C. for 15 minutes, followed by addition of Part G alcohol (10 g) in $CH_2Cl_2$ (100 ml) very slowly. Stirring was continued for 15 minutes at −78° C., then $Et_3N$ (17.5 ml) was added dropwise at −78° C. and the reaction was gradually warmed to room temperature. Water (100 ml) was added and the water layer separated was further extracted with $CH_2Cl_2$ (240 ml×2). The combined $CH_2Cl_2$ layers were washed with $H_2O$ (120 ml×3) and dried over $MgSO_4$. Filtration and evaporation of solvent gave a pale straw-colored oil, which was dried by azetropic distillation with benzene several times. Title aldehyde in the form of a pale straw-colored foam (10.1 g) was obtained. This was used for the subsequent reaction without any purification.

J (and J')
(Z)-7-[(cis)-2[(S*)-2,2-Dimethyl-1,3-dioxolan-4-yl]-6-[(methylsulfonyl)oxy]-2-cyclohexen-1-yl]-5-heptenoic acid, methyl ester (J)

To (4-carboxybutyl)triphenylphosphonium bromide (15.948 g, 36 mmole) suspended in THF (150 ml) was added KO t-amylate in toluene (1.6M, 45 ml) dropwise at room temperature. After stirring for 6 hours at room temperature, a burgundy colored solution was obtained. Part H aldehyde (crude product, 10.1 g, 24 mmole) dissolved in THF (20 ml) was cooled to −30° C.~ −40° C. The ylid solution (190 ml) was added dropwise over 40 minutes. The reaction was stirred at −40° C. for one hour and at room temperature overnight. The reaction was quenched with saturated $NH_4Cl$ (40 ml) and brine (50 ml). The products were extracted with EtOAc (40 ml, 200 ml×3), which was dried over $MgSO_4$. Filtration and evaporation of solvents gave a straw-colored oil (15.3 g). This was suspended in $Et_2O$ and treated with $CH_2N_2$ until the desired acid was esterified. The solvent was evaporated off in vacuo and the residue was purified by $SiO_2$ column (silica 60, 300 g) eluted with $Et_2O$/petroleum ether=1/1 and $Et_2O$ to give title compound (4.8 g, 11.52 mmole, 48%). Depending upon the amount of the ylid used, compound (Z)-7-[(1α,2α,3α,6α)-2-[(S*)-2,2- dimethyl-1,3-dioxolan-4-yl]-3,6-bis-[(methylsulfonyl)oxy]cyclohexyl]-5-heptenoic acid, methyl ester (J') can be obtained.

K.
(Z)-7-[(cis)-2-[(S*)-1,2-Dihydroxyethyl]-6-[(methylsulfonyl)oxy]cyclohexyl]-5-heptenoic acid, methyl ester To Part J compound (5.59 g, ca. 13.45 mmole) dissolved in MeOH (56 ml) was added p-TsOH.H$_2$O (140 mg, 0.73 mmole), and the reaction was stirred at room temperature overnight. Saturated NaHCO$_3$ (10 ml) was added and MeOH was removed in vacuo. The residue was partitioned between EtOAc (100 ml) and brine (50 ml). The water layer was further extracted with EtOAc (100 ml × 2). The combined EtOAc layers were washed with brine (50 ml) and dried over MgSO$_4$. Filtration and evaporation of solvent gave an oil (5.723 g), which was purified by SiO$_2$ column (silica 60, 150 g) eluted with 5% MeOH in CH$_2$Cl$_2$ to give the starting material (1.1 g, 2.6 mmole) and the desired title diol (3.5 g, 9.2 mmole, ca. 85%).

L.
(Z)-7-[(cis)-2-Formyl-6-[(methylsulfonyl)oxy]-2-cyclohexen-1-yl]-5-heptenoic acid, methyl ester NaIO$_4$ (2.19 g, 10.1 mmole) suspended in H$_2$O (4 ml) was added to Part K diol (3.5 g, 9.2 mmole) in MeOH (36 ml) at 0° C. Stirring was continued for 1.5 hours at room temperature. 10% Na$_2$S$_2$O$_3$ (10 ml) was added to the reaction. The reaction was stirred for 10 minutes, and poured into Et$_2$O (100 ml) and H$_2$O (20 ml). The products were extracted into Et$_2$O layer. The water layer was further extracted with Et$_2$O (50 ml × 3). The combined Et$_2$O layers were washed with brine (50 ml) and dried over MgSO$_4$. Filtration and evaporation of solvents gave a pale yellow oil (3.1 g). The crude products were used for the subsequent reaction.

M.
(Z)-7-[(1α,2α,3α,6α)-3-(Acetylthio)-2-(dimethoxymethyl)-6-[(methylsulfonyl)oxy]cyclohexyl]-5-heptenoic acid, methyl ester CH$_3$COSH (9 ml, 0.102 mole) and Et$_3$N (9 ml, 0.065 mole) were added to the crude Part L product (3.1 g, 9 mmole) in CH$_2$Cl$_2$ (230 ml) at −20° C. The reaction was stirred for four hours at −20° C. ∼ −10° C. and one hour at −10°∼0° C. The reaction was poured into saturated NaHCO$_3$ and the products were extracted into CH$_2$Cl$_2$. The water layer was further extracted with CH$_2$Cl$_2$ (100 ml × 3). The combined CH$_2$Cl$_2$ layers were washed with saturated NaHCO$_3$ and brine and dried over MgSO$_4$. Filtration and evaporation of solvent gave an oil (4.1 g). The crude oil (4.1 g) was dissolved in MeOH [300 ml, dried over Mg(OMe)$_2$] and treated with p-TsOH.H$_2$O (240 mg, 1.26 mmole) overnight at room temperature. NaHCO$_3$ (1.2 g) in H$_2$O (5 ml) was added to the reaction and MeOH was mostly removed in vacuo. The residue (∼10 ml) was poured into Et$_2$O (150 ml) and H$_2$O (30 ml). The products were extracted into Et$_2$O layer. The water layer was further extracted with Et$_2$O (100 ml × 2). The combined Et$_2$O layers were washed with brine (50 ml) and dried over MgSO$_4$. Filtration and evaporation of solvent gave a pale yellow oil (4.2 g) which was purified by SiO$_2$ column (silica 60, 120 g) eluted with Et$_2$O/petroleum ether = 1/1 and Et$_2$O/petroleum ether = 2/1, to give desired title acetal (3.01 g, 6.4 mmole, 70% from Part H diol).

N.
(Z)-7-[(cis)-5-(Acetylthio)-6-(dimethoxymethyl)-1-cyclohexen-1-yl]-5-heptenoic acid, methyl ester To Part M mesylate (3.01 g, 6.43 mmole) dissolved in toluene (30 ml) was added 1,8-diazabicyclo[5.4.0]-undec-7-ene (DBU) (5.5 g, 36 mmole). The reaction was warmed to 80° C. under magnetic stirring for 18 hours. The reaction was poured into Et$_2$O (130 ml) and washed with 0.5N-HCl (30 ml). The HCl wash was re-extracted with Et$_2$O (70 ml). The combined Et$_2$O layers were washed with 0.5N-HCl (30 ml), H$_2$O (30 ml × 3) and dried over MgS$_4$. Filtration and evaporation of the solvent gave a straw-colored oil (2.4 g), which was purified by SiO$_2$ column (silica 60, 80 g) eluted with Et$_2$O/petroleum ether = ½ to give title thioacetate (1.41 g, 3.8 mmole, 58%) and disulfide described in Part O (0.58 g, 1.6 mmole, 25%) as colorless oils.

O.
5,5'-Bis[[(Z)-7-[(cis)-6-(dimethoxymethyl)-1-cyclohexen-1-yl]-7-heptenoic acid, methyl ester]disulfide Solid NaOMe (84 mg, 1.6 mmole) was added to a magnetically stirred solution of Part N thioacetate (580 mg, 1.6 mmole) in MeOH (58 ml) at room temperature. Hydrolysis of thioacetate was completed in 2 hours at room temperature. O$_2$ was then bubbled through the reaction for 2 days. Saturated NH$_4$Cl (10 ml) and saturated CuSO$_4$ (100 μl) were added and O$_2$ was again bubbled through the reaction to complete disulfide formation. The reaction was concentrated in vacuo to remove most of MeOH. The products were extracted with Et$_2$O (100 ml, 50 ml). The combined Et$_2$O layers were washed with H$_2$O (30 ml × 2) and dried over MgSO$_4$. Filtration and evaporation of the solvent gave a straw-colored oil (530 mg) which was purified by SiO$_2$ column (silica 60, 30 g) eluted with Et$_2$O/petroleum ether ¼∼½ to give the desired title disulfide (452 mg, 0.69 mmole, 85%) as a colorless oil.

Anal Calcd for C$_{34}$H$_{54}$O$_8$S$_2$: C, 62.35; H, 8.31; S, 9.79; Found: C, 62.28; H, 8.19; S, 9.77.

P.
[1β,2α(E),3α,4β]-7-[2-Chloro-3-(dimethoxymethyl)-7-thiabicyclo[2.2.1]hept-2-yl]-5-heptenoic acid, methyl ester SO$_2$Cl$_2$ (63 μl, 0.784 mmole) in CH$_2$Cl$_2$ (5 ml) was added dropwise to a magnetically stirred solution of Part O disulfide (515 mg, 0.783 mmole) in CH$_2$Cl$_2$ (7.8 ml) at −78° C. over 30 minutes. Stirring was continued for 2 hours at −78° C., 10% Na$_2$S$_2$O$_3$ (10 ml) and saturated NaHCO$_3$ (10 ml) were added and the reaction was warmed to room temperature. The reaction was poured into CH$_2$Cl$_2$ (50 ml) and the products were extracted into CH$_2$Cl$_2$ layer. The water layer was further extracted with CH$_2$Cl$_2$ (50 ml × 2). The combined CH$_2$Cl$_2$ layers were washed with H$_2$O (30 ml × 2) and dried over MgSO$_4$. Filtration and evaporation of solvent gave a colorless oil (568.5 mg, quantitative recovery).

Q.
[1β,2α(Z),3α,4β]-7-[3-(Dimethoxymethyl)-7-thiabicyclo[2.2.1]hept-2-yl]-5-heptenoic acid, methyl ester ZnCl$_2$ (313.2 mg, 2 mmole) and NaCNBH$_3$ (285 mg, 4 mmole) were dried under vacuum and heat (∼50°-6° C.) for 20 minutes. Then Et$_2$O (20 ml) was added and the reaction was stirred for 30 minutes at room temperature, followed by an addition of Et$_3$N (320 μl, 2.3 mmole). After 30 minutes stirring at room temperature, Part P chloride (crude products, 568.5 mg) in Et$_2$O (10 ml) was added at room temperature. The reaction was stirred overnight at room temperature. Saturated NaHCO$_3$ (3 ml) was added and the reaction was poured into Et$_2$O (100 ml). The products were extracted into Et$_2$O layer. The water layer was further extracted with Et$_2$O (100 ml). The combined Et$_2$O layers were washed with saturated NaHCO$_3$ (25 ml), H$_2$O (25 ml×2) and dried over MgSO$_4$. Filtration and evaporation of the solvent gave the desired title product (379 mg, 1.155 mmole, 74% from Part O disulfide.

Anal Calcd for C$_{17}$H$_{28}$O$_4$S: C, 62.16; H, 8.59; S, 9.76; Found: C, 62.13; H, 8.42; S, 9.67.

R.
[1α,2β(5Z),3β,4α)]-7-[3-Formyl-7-thiabicyclo[2.2.1-]hept-2-yl]-5-heptenoic acid, methyl ester CF$_3$CO$_2$H (3.5 ml) was added to a magnetically stirred solution of Part Q acetal (403 mg, 1.22 mmole) in acetone (9 ml) and 37% formaline (25 ml) at 0° C. Stirring was continued at 0° C. for 8.5 hours. Saturated NaHCO$_3$ was added until no CO$_2$ gas evolution was observed. The products were extracted with Et$_2$O (70 ml×3). The combined Et$_2$O layers were washed with H$_2$O (40 ml×3) and dried over MgSO$_4$. Filtration and evaporation of the solvent gave a colorless oil (400 mg), which was purified by SiO$_2$ column (silica 60, 20 g) eluted with 10% Et$_2$O in petroleum ether to give title aldehyde (266.8 mg, 0.939 mmole, 77%) as a colorless oil.

S.
[1α,2β(5Z),3β,4α]-7-[3-[[2-[(Phenylamino)carbonyl]hydrazono]methyl]-7-thiabicyclo[2.2.1]hept-2-yl]-5-heptenoic acid, methyl ester The aldehyde from Part R (51.3 mg, 0.18 mmole) was dissolved in EtOH (3.5 ml). 4-Phenylsemicarbazide (54 mg, 0.36 mmole) was added. The reaction was stirred at room temperature overnight. The solvent was evaporated off in vacuo and the residue was purified by SiO$_2$ column (silica 60, 4 g) eluted with Et$_2$O/petroleum ether=1/1 to give title semicarbazone (70.3 mg, 0.168 mmole, 93%) as a colorless oil.

T.
[1α,2β(5Z),3β,4α]-7-[3-[[2-[(Phenylamino)carbonyl]hydrazino]methyl]-7-thiabicyclo[2.2.1]hept-2-yl]-5-heptenoic acid, methyl ester Acetic acid (0.6 ml) was added dropwise to a magnetically stirred solution of Part S semi-carbazone (70.3 mg, 0.168 mmole) and NaCNBH$_3$ (20.9 mg, 0.337 mmole) in MeOH (2 ml) at room temperature. Stirring was continued at room temperature overnight. EtOAc (20 ml) and saturated NaHCO$_3$ (10 ml) were added. The products were extracted into EtOAc. The water layer was further extracted with EtOAc (10 ml×2). The combined EtOAc layers were washed with 1N-NaOH (5 ml×2) and brine until the wash became neutral. The organic layer was dried over MgSO$_4$. Filtration and evaporation of the solvent gave a colorless oil (71.9 mg). The oil was purified by SiO$_2$ column (silica 60, 3 g) eluted with 2% MeOH in CH$_2$Cl$_2$ to give title methyl ester (53.8 mg, 0.129 mmole, 77%) as a colorless oil.

EXAMPLE 2
[1α,2β(5Z),3β,4α]-7-[3-[[2-[(Phenylamino)carbonyl]hydrazino]methyl]-7-thiabicyclo[2.2.1]hept-2-yl]-5-heptenoic acid To Example 1 methyl ester (53.8 mg) dissolved in THF (6 ml) were added 1N-LiOH (1.3 ml) and H$_2$O (1.3 ml). The reaction was stirred at room temperature for 6½ hours. After addition of 1N-HCl (1.3 ml), the water layer was saturated with solid KCl and the layers were separated. The water layer was further extracted with Et$_2$O (20 ml×3). The combined organic layers were washed with brine (10 ml) and dried over MgSO$_4$. Filtration and evaporation of the solvents gave a slightly yellow colored oil (53.2 mg) which was purified by HPLC (50μ silica gel, semi-prep column) eluted with 2–5% MeOH in CH$_2$Cl$_2$ to give title acid (44.3 mg) as a colorless glass. This was crystallized from MeOH/diisopropyl ether to give title compound in the form of white solids, (36.5 mg, 0.0906 mmole, 70%). TLC: silica gel, 6% MeOH in CH$_2$Cl$_2$, R$_f$=0.28, PMA.

Anal Calcd for C$_{21}$H$_{29}$N$_3$O$_3$S: C, 62.47; H, 7.24; N, 10.45; S, 7.94; Found: C, 62.34; H, 7.28; N, 10.20; S, 7.70.

EXAMPLE 3
(1α,2β,3β,4α)-7-[3-[[2-[(Phenylamino)carbonyl]hydrazino]methyl]-7-thiabicyclo[2.2.1]hept-2-yl]heptanoic acid

A.
(1α,2β,3β,4α)-7-[3-Dimethoxymethyl)-7-thiabicyclo[2.2.1]hept-2-yl]heptanoic, methyl ester 10% Pd/C (20 mg) was added to a magnetically stirred solution of the compound prepared in Example 1 Part O (401 mg, 1.22 mmole) in EtOAc under nitrogen. The atmosphere was replaced with hydrogen and the compound was hydrogenated at atmospheric pressure overnight. The reaction was filtered through a celite pad, which was washed with EtOAc (10 ml×b 3). The filtrate and the washes were combined, and concentrated to dryness. The resulting colorless oil was purified by silica gel column (Baker silica gel for flash chromatography, 15 g) eluted with Et$_2$O/petroleum ether=¼ to give the desired titled compound (400 mg, 1.22 mmole, quant.).

B.
(1α,2β,3β,4α)-7-[3-Formyl-7-thiabicyclo[2.2.1]hept-2-yl]heptanoic acid, methyl ester Following the procedure of Example 1 Part R, except substituting the part A acetal for the Example 1 Part Q acetal, the title compound is obtained.

C.
(1α,2β,3β,4α)-7-[3-[[2-[(Phenylamino)carbonyl]hydrazino]methyl]-7-thiabicyclo[2.2.1]hept-2-yl]heptanoic acid Following the procedure of Examples 1 and 2 except substituting the Part B aldehyde for the Example 1 Part R aldehyde, the title product is obtained.

EXAMPLE 4

[1α,2β(5Z),3β,4α]-7-[3-[2-[2-[(Phenylamino)carbonyl]hydrazino]ethyl]-7-thiabicyclo[2.2.1]hept-2-yl]-5-heptenoic acid

A.

[1β,2α(5Z),3α,4β]-7-[3-[(2-Oxo)ethyl]-7-thiabicyclo[2.2.1]hept-2-yl]-5-heptenoic acid, methyl ester Into a dry 100 ml round bottom 3-necked flask containing a stir bar is added dried 12.9 g (37.7 mmoles) methoxymethyltriphenylphosphonium chloride $((C_6H_5)_3P^+{-}CH_2OCH_3Cl^-)$ and 235 ml distilled toluene (stored over molecular sieves). The resulting suspension is stirred in an ice-bath, under argon, until cold and then a 1.55M solution of 18.3 ml (28.3 mmol) of potassium t-amylate in toluene is added dropwise. A bright red solution formed which is stirred at 0° C. for an additional 35 minutes. Thereafter, a solution of 4.97 g (18.8 mmol) [1α,2β(5Z),3β,4α]-7-[3-formyl-7-thiabicyclo[2.2.1]hept-2-yl]-5-heptenoic acid, methyl ester in 60 ml toluene is added by means of a dropping funnel over a 35 minute period with the ice-bath still in place. The reaction is then quenched by addition of 2.3 g (39 mmol) acetic acid in 5 ml ether. The reaction mixture immediately turns pale yellow and is immediately poured into 200 ml saturated $NH_4Cl$, and extracted with ether (4×200 ml). The combined ether phases are washed with NaCl saturated solution, and dried ($MgSO_4$) and concentrated to yield a yellow oil in a white crystalline solid (phosphine oxide). The white solid is triturated with EtOAc and the mother liquor is purified by chromatography on an LPS-1 silica column. The fractions obtained are (A) [1α,2β(5Z),3β,4α]-7-[3-(2-oxo)ethyl-7-thiabicyclo[2.2.1]hept-2-yl]-5-heptenoic acid, methyl ester, (B) [1α,2β(5Z),3β,4α]-7-[3-(2-methoxy)ethenyl]-7-thiabicyclo[2.2.1]hept-2-yl]-5-heptenoic acid, methyl ester, and (C) [1α,2β(5Z),3β,4α]-7-[3-(2,2-dimethoxy)ethyl-7-thiabicyclo[2.2.1]hept-2-yl]-5-heptenoic acid, methyl ester.

Compounds (B) and (C) are each treated with trifluoroacetic acid to convert each to compound (A).

B.

[1α,2β(5Z),3β,4α]-7-[3-[2-[2-[(Phenylamino)carbonyl]hydrazino]ethyl]-7-thiabicyclo[2.2.1]hept-2-yl]-5-heptenoic acid Following the procedure of Examples 1 and 2 except substituting the above part A aldehyde for the aldehyde used in Example 1, Part R, the title compound is obtained.

EXAMPLE 5

[1α,2β(5Z),3β,4α]-7-[3-[4-[2-[(Phenylamino)carbonyl]hydrazino]butyl]-7-thiabicyclo[2.2.1]hept-2-yl]-5-heptenoic acid

A.

[1α,2β(5Z),3β,4α]-7-[3-(3-Oxo)propyl-7-thiabicyclo[2.2.1]hept-2-yl]-5-heptenoic acid, methyl ester Following the procedure of Example 4, part A except substituting [1α,2β(5Z),3β,4α]-7-[3-(2-oxo)ethyl-7-thiabicyclo[2.2.1]hept-2-yl]-5-heptenoic acid, methyl ester for [1α,2β(5Z),3β,4α]-7-[3-formyl-7-thiabicyclo[2.2.1]hept-2-yl]-5-heptenoic acid, methyl ester, the title A compound is obtained.

B.

[1α,2β(5Z),3β,4α]-7-[3-(4-Oxo)butyl-7-thiabicyclo[2.2.1]hept-2-yl]-5-heptenoic acid, methyl ester Following the procedure of Example 4, part A, except substituting the aldehyde from part A above, for [1α,2β(5Z),3β,4α]-7-[3-formyl-7-thiabicyclo[2.2.1]hept-2-yl]-5-heptenoic acid, methyl ester, the title B aldehyde is obtained.

C.

[1α,2β(5Z),3β,4α]-7-[3-[4-[[(Phenylamino)carbonyl]hydrazino]butyl]-7-thiabicyclo[2.2.1]hept-2-yl]-5-heptenoic acid Following the procedure of Examples 1 and 2, except substituting the above part B aldehyde for the aldehyde used in Example 1, the title compound is obtained.

EXAMPLE 6

Tris(hydroxymethyl)aminomethane salt of [1α,2β(5Z),3β,4α]-7-[3-[[[2-(Phenylamino)carbonyl]hydrazino]methyl]-7-thiabicyclo[2.2.1]hept-2-yl]-5-heptenoic acid A solution of the compound formed in Example 2 in methanol is treated with an equivalent amount of tris(hydroxymethyl)aminomethane. The solvent is removed by evaporation to yield the title compound.

EXAMPLES 7 TO 26

Following the procedure of Examples 1 and 2 except substituting for (4-carboxybutyl)triphenylphosphonium bromide in Example 1 Part G the phosphonium compound shown in Column I of Table A set out below and substituting for 4-phenylsemicarbazide in Example 1 Part P, the semicarbazide shown in Column II of Table A set out below, the product shown in Column III is obtained.

TABLE A

| Ex. No. | Column I<br>$(C_6H_5)_3P{-}CH_2{-}(CH_2)_m{-}CO_2H$<br>$(CH_2)_m$ | Column II<br>$H_2NNHC(O){-}X{-}R^1$<br>$X{-}R^1$ | Column III<br>$CH_2{-}CH{=}CH{-}(CH_2)_m{-}CO_2H$ / $CH_2{-}NH{-}NH{-}C(O){-}X{-}R^1$ | |
|---|---|---|---|---|
| | | | $(CH_2)_m$ | $X{-}R^1$ |
| 7. | $(CH_2)_4$ | $NH_2$ | As in Column I | As in Column II |
| 8. | $-CH_2-CH(CH_3)-$ | $NH{-}C_6H_5$ | | |

TABLE A-continued

| Ex. No. | Column I (C₆H₅)₃P—CH₂—(CH₂)ₘ—CO₂H (CH₂)ₘ | Column II H₂NNHC(O)—X—R¹ X—R¹ | Column III (bicyclic hydrazide structure) (CH₂)ₘ / X—R¹ |
|---|---|---|---|
| 9 | —CH₂—C(CH₃)₂—CH₃ | NH—C₄H₉ | |
| 10 | —CH(CH₃)—CH₂—CH(CH₃) | NH—CH₃ | |
| 11 | —(CH₂)₅— | NH—CH₂C₆H₅ | |
| 12 | —(CH₂)₆— | NH—CH₂-cyclohexyl | |
| 13 | —(CH₂)₂— | NH-cyclopentyl | |
| 14 | —CH₂— | NHC₃H₇ | |
| 15 | —CH₂— | O—C₄H₉ | |
| 16 | —(CH₂)₂— | O—C₅H₁₁ | |
| 17 | —(CH₂)₃— | O—C₆H₁₃ | |
| 18 | —CH₂—CH(CH₃)— | O—(CH₂)₂—C₆H₅ | |
| 19 | —CH₂—C(CH₃)₂— | O—CH₂-cyclopentyl | |
| 20 | —CH(CH₃)—CH₂— | O-cyclohexyl | |
| 21 | —C(CH₃)₂—CH₂— | CH₃ | |
| 22 | —C(CH₃)₂—CH₂—C(CH₃)₂— | CH₂-phenyl | |
| 23 | —(CH₂)₂— | CH₂-cyclopentyl | |
| 24 | —CH₂—CH(CH₃)— | CH₂—CH₂-cyclohexyl | |

TABLE A-continued

| Ex. No. | Column I (C$_6$H$_5$)$_3$P—CH$_2$—(CH$_2$)$_m$—CO$_2$H (CH$_2$)$_m$ | Column II H$_2$NNHC(O)—X—R$^1$ X—R$^1$ | Column III (structure with CH$_2$—CH=CH—(CH$_2$)$_m$—CO$_2$H and CH$_2$—NH—NH—C(O)—X—R$^1$) (CH$_2$)$_m$ / X—R$^1$ |
|---|---|---|---|
| 25. | —CH$_2$—C(CH$_3$)$_2$—CH$_3$ | CH$_2$—C$_6$H$_13$ | |
| 26. | —CH(CH$_3$)—CH(CH$_3$)— | CH$_2$—(CH$_2$)$_3$—C$_6$H$_5$ | |

What is claimed is:

1. A compound having the structural formula

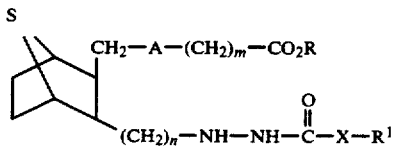

and including all stereoisomers thereof, wherein A is —CH=CH— or —(CH$_2$)$_2$—;
m is 1 to 8; n is 1 to 4;
R is hydrogen, lower alkyl, alkali metal, or a polyhydroxylamine salt; X is O, CH$_2$ or NH; R$^1$ is H (where X≠O), lower alkyl, aryl, aralkyl, cycloalkyl or cycloalkylalkyl, wherein the term aryl by itself or as part of another group contains 6 to 10 carbons and is phenyl or naphthyl, each of which is unsubstituted or substituted with 1 or 2 lower alkyl groups, 1 or 2 halogens, 1 or 2 lower alkoxy groups, 1 or 2 hydroxy groups, 1 or 2 alkylamino groups, 1 or 2 alkanoylamino groups, 1 or 2 arylcarbonylamino groups, 1 or 2 amino groups, 1 or 2 nitro groups, 1 or 2 cyano groups, 1 or 2 thiol groups and/or 1 or 2 alkylthio groups.

2. The compound as defined in claim 1 wherein A is —CH=CH—.

3. The compound as defined in claim 1 wherein R is H.

4. The compound as defined in claim 1 wherein n is 1.

5. The compound as defined in claim 1 wherein n is 2.

6. The compound as defined in claim 1 wherein X is NH.

7. The compound as defined in claim 1 wherein A is —CH=CH—, m is 2 to 4, n is 1 or 2, R is H, X is NH, and R$^1$ is lower alkyl, aryl or cycloalkyl.

8. The compound as defined in claim 1 wherein A is —CH=CH—, m is 3, n is 1, R is H or CH$_3$, X is NH, and R$^1$ is phenyl.

9. The compound as defined in claim 1 having the name [1α,2β(5Z),3β,4α]-7-[3-[[2-(phenylamino)carbonyl]hydrazino]methyl]-7-thiabicyclo[2.2.1]hept-2-yl]-5-heptenoic acid or its methyl ester.

10. A composition for inhibiting platelet aggregation and bronchoconstriction comprising an effective amount of a compound as defined in claim 1 or a pharmaceutically acceptable salt thereof, and a pharmaceutically acceptable carrier thereof.

11. A method of inhibiting platelet aggregation and bronchoconstriction, which comprises parenterally administering to the circulatory system of a mammalian host an effective amount of a compound as defined in claim 1 or a pharmaceutically acceptable salt thereof.

12. The method as defined in claim 11 wherein said compound is administered in an amount within the range of from about 1 to about 100 mg/kg.

13. A method of inhibiting platelet aggregation which comprises administering to a mammalian host an effective amount of a compound as defined in claim 1 or a pharmaceutically acceptable salt thereof.

14. A method of inhibiting bronchoconstriction associated with asthma, which comprises administering to a mammalian host an effective amount of a compound as defined in claim 1 or a pharmaceutically acceptable salt thereof.

15. A method for inhibiting platelet aggregation and bronchoconstriction by blocking the action of thromboxane A$_2$ receptor, which comprises administering to a mammalian host an effective amount of a compound as defined in claim 1 or a pharmaceutically acceptable salt thereof.

* * * * *

UNITED STATES PATENT AND TRADEMARK OFFICE
CERTIFICATE OF CORRECTION

PATENT NO. : 4,588,741
DATED : May 13, 1986
INVENTOR(S) : Masami Nakane

It is certified that error appears in the above—identified patent and that said Letters Patent is hereby corrected as shown below:

On the title page, line 3 of the title, "Thiabicycloheptane" should read --7-Thiabicycloheptane--.
Column 1, line 3 of the title, "Thiabicycloheptane" should read --7-Thiabicycloheptane--.
Column 5, line 45, structure A should read

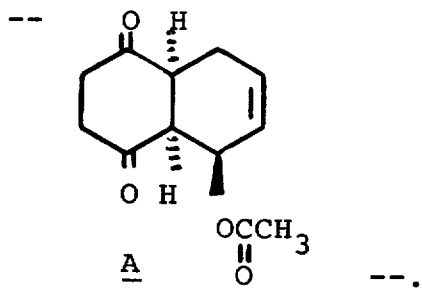

Column 6, line 5, structures D and E should read

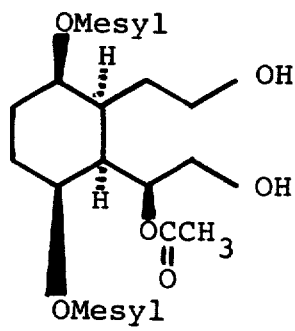 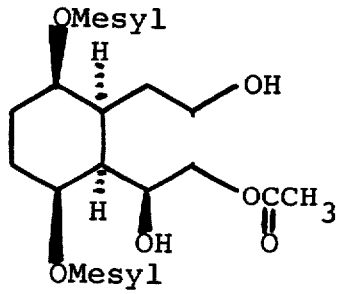

UNITED STATES PATENT AND TRADEMARK OFFICE
CERTIFICATE OF CORRECTION

PATENT NO. : 4,588,741

DATED : May 13, 1986

INVENTOR(S) : Masami Nakane

It is certified that error appears in the above—identified patent and that said Letters Patent is hereby corrected as shown below:

Column 6, line 55, structure H should read
--

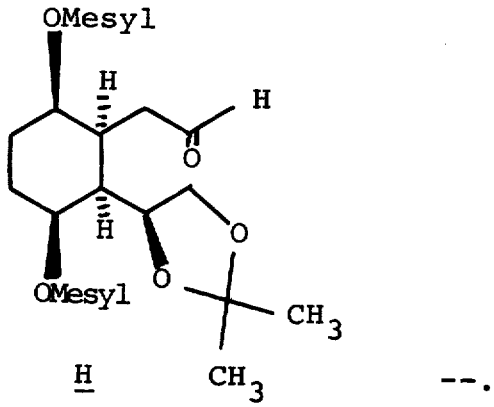

Column 16, line 45, "(10 ml x b 3)" should read
--(10 ml x 3)--.

Signed and Sealed this

Fourth Day of November, 1986

[SEAL]

*Attest:*

DONALD J. QUIGG

*Attesting Officer*     *Commissioner of Patents and Trademarks*